(12) United States Patent
Tomiyama et al.

(10) Patent No.: US 6,635,622 B2
(45) Date of Patent: Oct. 21, 2003

(54) GLYCOLIPID DERIVATIVE

(75) Inventors: Hiroshi Tomiyama, Nagano-ken (JP); Takashi Yanagisawa, Koshoku (JP); Masayuki Nimura, Ueda (JP); Atsushi Noda, Nagano (JP); Tsuyoshi Tomiyama, Nagano-ken (JP)

(73) Assignee: Kotobuki Pharmaceutical Co., Ltd., Nagano-ken (JP)

( * ) Notice: Subject to any disclaimer, the term of this patent is extended or adjusted under 35 U.S.C. 154(b) by 49 days.

(21) Appl. No.: 09/878,425

(22) Filed: Jun. 12, 2001

(65) Prior Publication Data

US 2002/0032158 A1 Mar. 14, 2002

(30) Foreign Application Priority Data

Jun. 12, 2000  (JP) ......................... 2000-175320

(51) Int. Cl.[7] ......................... A61K 31/70; C07H 17/00; C07H 5/06
(52) U.S. Cl. ..................... 514/25; 514/23; 514/24; 514/42; 536/17.5; 536/17.9; 536/18.7; 536/29.1
(58) Field of Search ............... 536/17.5, 17.9, 536/18.7, 29.1; 514/23, 24, 25, 42

(56) References Cited

PUBLICATIONS

Hasegawa, A. et al. Synthetic Studies on Sialoglycoconjugates. 20. Synthesis of Cerebroside Lactosyl Ceramide, and Ganglioside GM3 Analogs Containing beta–Thioglycosidically Linked Ceramide. Carbohydrate Research 1991, 214(1), 43–53.*

Bessanov, V.V. et al. Synthesis of Thioglycosphingolipids. Bioorg. Khim. 1991, 17(3), 403–409.*

* cited by examiner

*Primary Examiner*—Kathleen K. Fonda
(74) *Attorney, Agent, or Firm*—Sherman & Shalloway

(57) ABSTRACT

The present invention is a compound of general formula (I) or a pharmaceutically acceptable salt of,

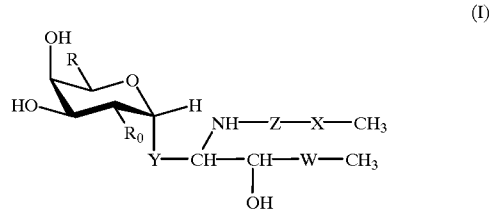

(I)

wherein W represents carbon chain from 9 to 17 which containing double bond or hydroxy group occasionally; X represents carbon chain from 11 to 25 which containing double bond or hydroxy group occasionally; Y represents $-(CH_2)a-CH=CH-(CH_2)a'-$, $-(CH_2)a-$ (a, a' denotes an integer of 0–5 and a+a' is 5 and under.), $-S(O)_{0-2}CH_2-$, $-NHCH_2-$; Z represents $-CO-$, $-SO_2-$; R represents $-CH_2OH$, $CO_2H$, $CH_2OCH_2CO_2SO_3H$; $R_0$ represents $-OH$, $-NH_2$, $-NHAc$.

8 Claims, No Drawings

GLYCOLIPID DERIVATIVE

BACKGROUND OF THE INVENTION

1. Field of the Invention

This invention relates to a novel glycolipid derivatives thereof which have effective anti-tumor activity and immunostimulating activity thereof and the production method thereof, further relates to a medicine composition containing the glycolipid derivatives thereof.

2. Description of the Prior Art

A glycolipid play important biological roles to cell deffarantation, proliferation, and navus cell growth. (Hakomori et al, Annu. Rev. Biochem. 1981, 50, 733–764.; Morita et al, Glycosphingolipids. 1985, 59–82, Elsevier Science Publishing Co., New York.). And, Morita et al (J. Med. Chem. 1991, 38, 2176.) and Kawano et al (Proc. Natl. Acad. Sci. USA. 1998, 95, 5690.) have been reported that alpha-galactosylceramides have effective anti-tumor activity and immunostimulating activity. Futhermore, Kawano et al (Science. 1997, 278, 1626–1629.) and Sakai et al (J. Med. Chem. 1999, 42, 1836–1841.) have been reported that alpha-galactosylceramides exhibit stronger antitumor activity and immunostimulating activity than beta-galactosylceramide.

However, when the galactosylceramide is administrated as a medicine, we expect that glycosyl bond is hydrolyzed by enzyme so as galactosidase which exist in a lysozome (Chen et al., Biochem. Biophys. Acta. 1993, 1170, 53–61). C-glycosides, that oxygen atom on a glycoside bond were exchanged to carbon atom, has been known as a stable sugar derivatives on a glycosidase metabolism (Linhardt et al., Tetrahedron. 1998, 54, 9913–9959; Levy et al., The Chemistry of C-Glycosides, Pergamon:Oxford, 1995; Postema et al, C-Glycoside Synthesis, CRC Press: Boca Raton, 1995). In addition, S-glycoside which exchange oxygen atom to sulfur atom on the glycoside bond (Rahman et al, In Studies in Natural Products Chemistry, Elsevier: New York, 1991; Vol. 8, 315–317; Defaye et al, J. Carbohydr. Chem. (UK) 1998, 30, 159–166.) and N-glycosides which oxygen atom were replaced by nitrogen atom (Stunkel et al., Prog. Leukocyte Biol. 1989, 9, 575–579.) have been also known.

As a synthesis of the C-glycosides [which] with oxygen on the glycoside bond of a galactosyl ceramide were replaced by carbon atom, synthesis of the beta-C-galactosyl ceramide has been only report (Dondoni et al., J. Org. Chem. 1991, 64, 5557–5564). However, synthesis of a alpha-C-galactosyl ceramide (alpha-compound) has not been reported. Owing to stabilities against alpha-galactosidase, the alpha-compounds which have alpha-C, N, or S-glycoside bond are expected more effective than the alpha-O-galactoside that is decomposed by a alpha-galactosidase. Thus, those compounds have a potent anti-cancer activity and an immunostimulating activity, furthermore, are stable against hydrolysis with glucosidase, acid, and base, and also able to keep at a room temperature for a long time.

3. Problems to be Solved by the Invention

The object of the present invention is the provision of the glycolipid derivatives exhibiting potent antitumor activity and immunostimulating activity, and having alpha-C, N, or S-glycoside bond for allowing to stand at room temperature for a long time, Thus, the glycolipid derivatives exhibit potent antitumor activity and immunostimulating activity than a known compound, and furthermore it is able to save at room temperature for long time and continue the activity for long time.

4. Methods for Solution of the Problems

As a result of that research a glyoclipid derivatives for the purpose of synthesis of anti-tumor agent and immunostimulating agent, we found that a glycolipid derivatives which is described in the general formula (I), exhibits a potent anti-tumor effect and immunostimulating effect.

DETAILED DESCRIPTION OF THE INVENTION

The present invention provides medical composition which containing the general formula (I) and its pharmaceutically acceptable salt as active ingredient.

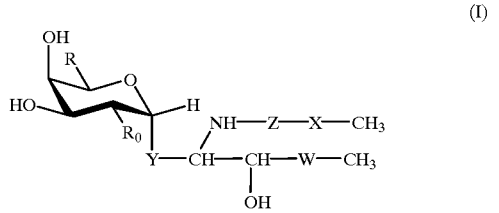

(I)

wherein W represents carbon chain from 9 to 17 which containing double bond or hydroxy group occasionally; X represents carbon chain from 11 to 25 which containing double bond or hydroxy group occasionally; Y represents $-(CH_2)_a-CH=CH-(CH_2)_{a'}-$, $-(CH_2)_a-$ (a,a' denotes an integer of 0–5 and a+a' is 5 and under [.]), $-S(O)_{0-2}CH_2-$, $-NHCH_2-$,; Z represents $-CO-$, $-SO_2-$; R represents $-CH_2OH$, $-CO_2H$, $-CH_2OCH_2CO_2H$, $-CH_2OSO_3H$; $R_0$ represents $-OH$, $-NH_2$, $-NHA_c$.

A preparing method of general formula (I) in the present invention are examplified and not restrict the disclosed invention. And, each sign are as mentioned above.

(A) Synthesis of the Ceramide Moiety

I. The ceramide precursor (A-1) is prepared by Schmidt's method (Liebigs Ann. 1995, 755–764) using D-galactose as a starting material. A primary hydroxy group of the compound (A-1) is tritylated, followed by benzylation of the secondary hydroxy group, and the conpound (A-2) is obtianed.

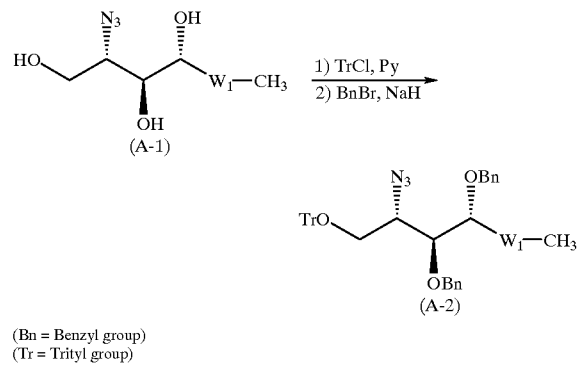

(Bn = Benzyl group)
(Tr = Trityl group)

(wherein $W_1$ is a carbon chain of C8 to C16 and it contains saturated position as the case may be.)

An azide group of the compound (A-2) is reduced by hydrogenatoin, or triphenylphosphine and water, thus the amino compound (A-3) is obtained.

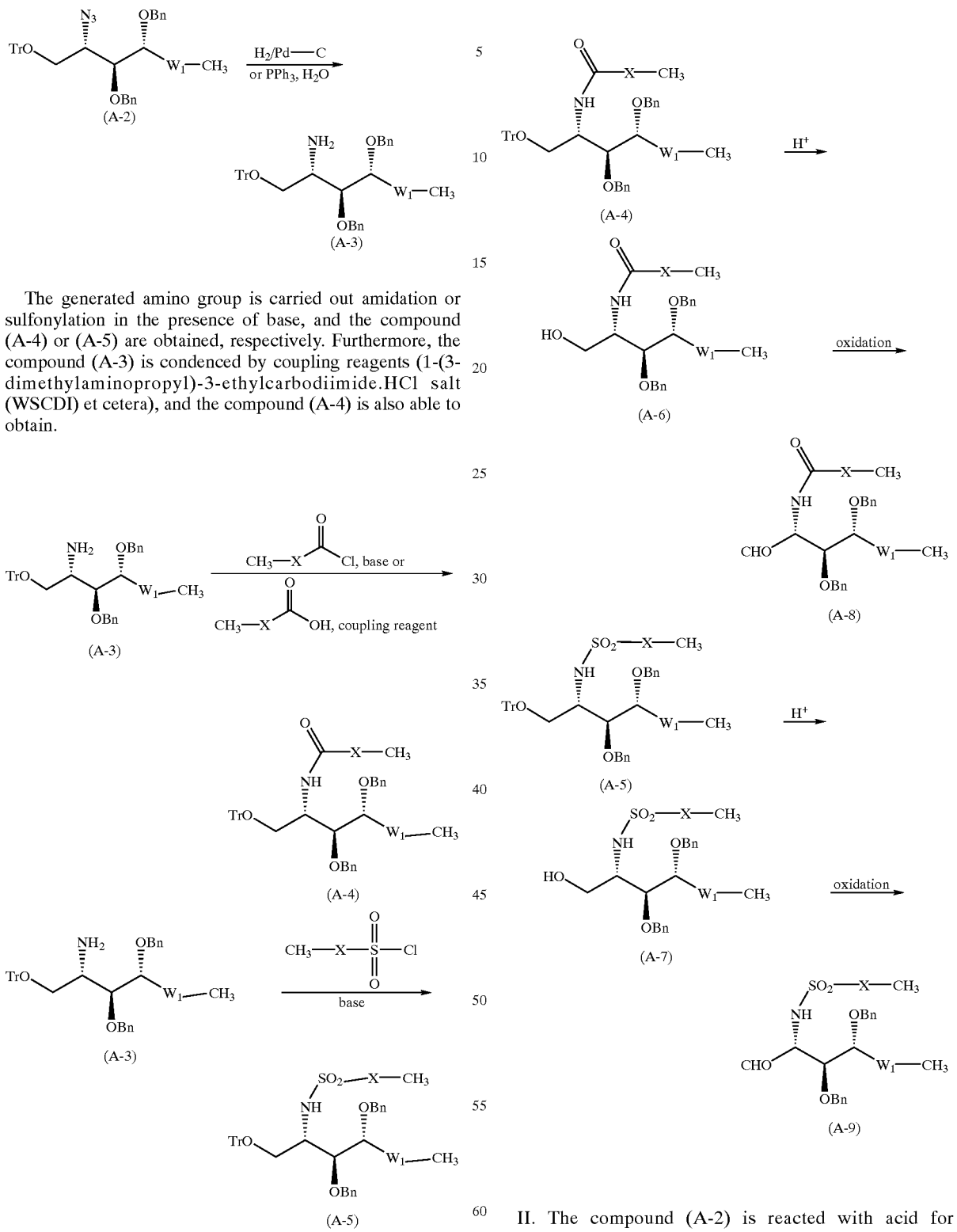

The generated amino group is carried out amidation or sulfonylation in the presence of base, and the compound (A-4) or (A-5) are obtained, respectively. Furthermore, the compound (A-3) is condenced by coupling reagents (1-(3-dimethylaminopropyl)-3-ethylcarbodiimide.HCl salt (WSCDI) et cetera), and the compound (A-4) is also able to obtain.

The compound (A-4) or (A-5) are reacted with acid for detritylation, to yield the compound (A-6) or (A-7). Then the generated hydroxy group is oxidized (Swern oxidation (J. Org. Chem. 1978, 43, 2482) etc), to yield the aldehyde compound (A-8) or (A-9).

II. The compound (A-2) is reacted with acid for detritylation, followed by a reduction ($PPh_3/H_2O$ etc) of an azide group, to yield the compound (A-10). Then amino group of the compound (A-10) is protected with Boc group, followed by an oxidation of the primary hydroxy group (Swern oxidation (J. Org. Chem. 1978, 43, 2482) etc), to yield the aldehyde compound (A-11).

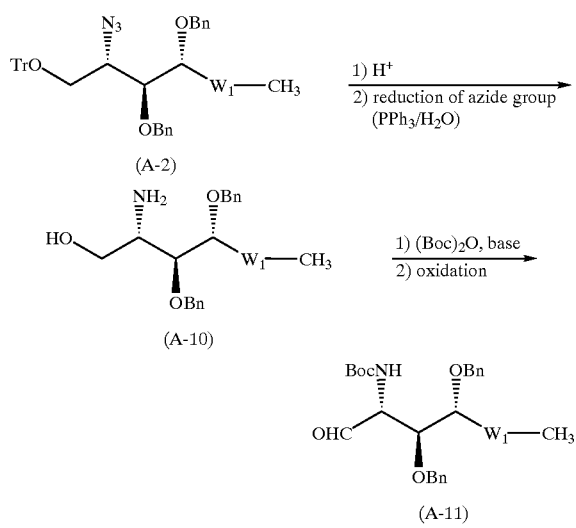

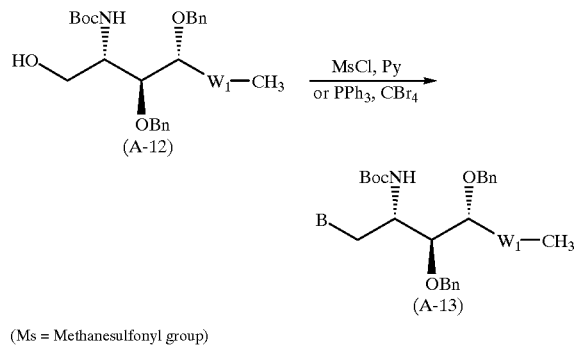

III. A primary hydroxy group of the compound (A-12) is carried out methanesulfonylation or bromination, to yield the compound (A-13).

(Ms = Methanesulfonyl group)

(B) Synthesis of the Sugar Moiety

A cyano group of galactosylcyano compound (B-1) is reduced by Lopex's procedure (J. Carbohydr. Chem. 1987, 6, 273–279), to yield the alcohol compound (B-2).

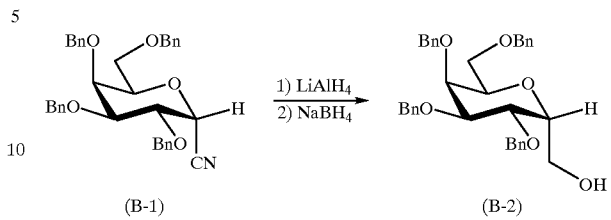

A primary hydroxy group of the compound (B-—2) is carried out tosylation followed by iodation, to yield the compound (B-3). Then it is reacted with triphenylphosphine, to yield the compound (B-4).

The compound (B-4) is reacted with base (n-butyl lithium, potassium fluoride, etc), to yield the compound (B-5).

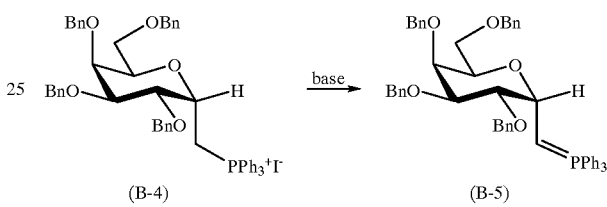

(C) Coupling Reaction with the Sugar Moiety and the Ceramide Moiety

I. The ceramide compound (A-8) and (A-9) which was prepared by the method (A), is carried out Wittig reaction with the compound (B-5) which was prepared by the method (B), to yield the compound (C-1) or (C-2) Then, those are reacted with sodium metal in liquid ammonia to yield the compound (C-3) or (C-4) Furthermore, those are hydrogenated to yield the compound (C-5) or (C-6). As another method, the compound (C-1) and (C-2) are directly hydrogenated to yield the compound (C-5) or (C-6).

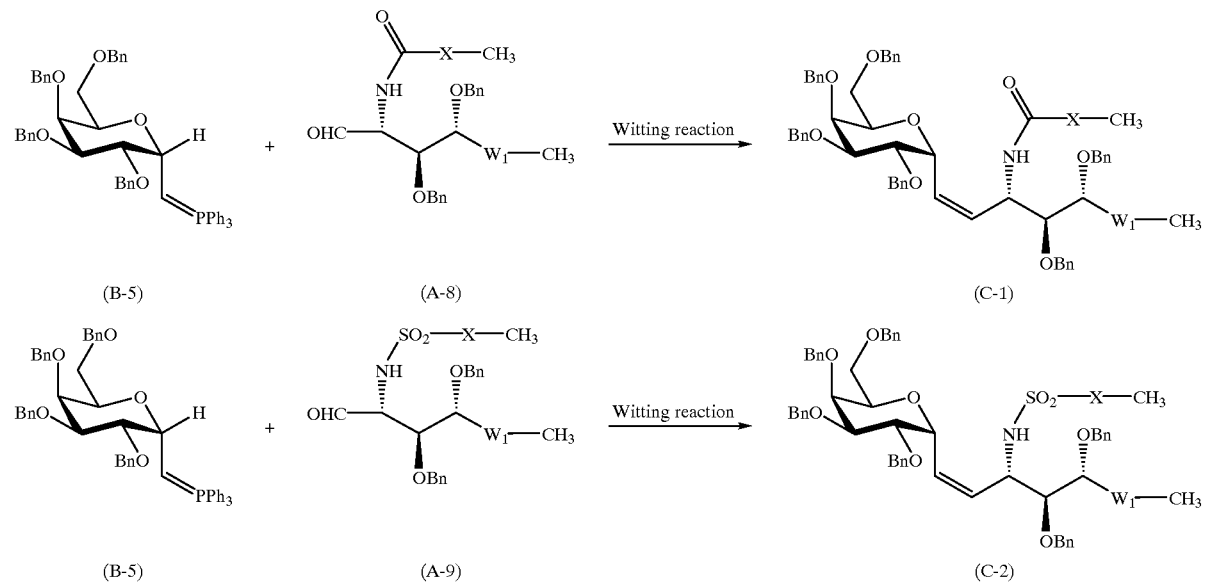

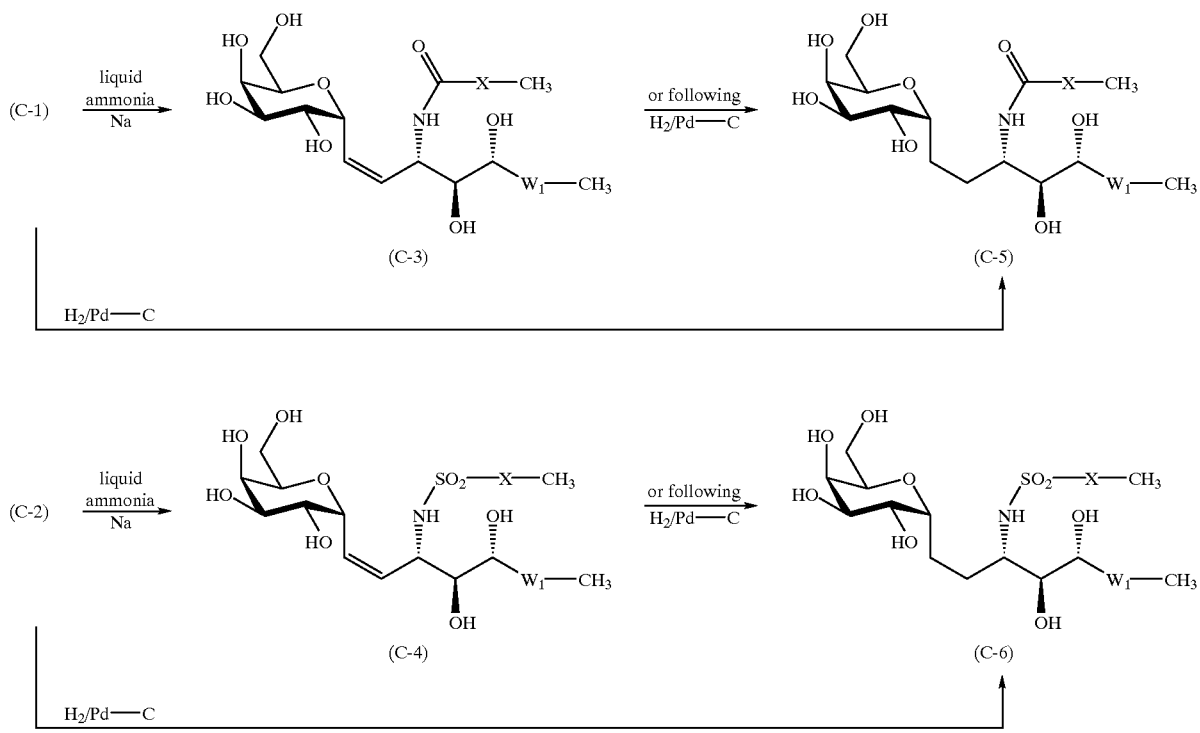

II. The ceramide compound (A-11) which was prepared by the method (A), is carried out wittig reaction with the compound (B-5) which was prepared by the method (B), to yield the compound (C-7). Then, it is reacted with a sodium metal in liquid ammonia to yield the compound (C-8). Furthermore, it is hydrogenated to yield the compound (C-9). As another method, the compound (C-7) is directly hydrogenated to yield the compound (C-9).

The compound (C-8) or (C-9) is reacted with acid for deprotection to yield the compound (C-10) or (C-11), then the amino group is carried out amidation or sulfonylation to yield the compound (C-3), (C-4), (C-5), or (C-6).

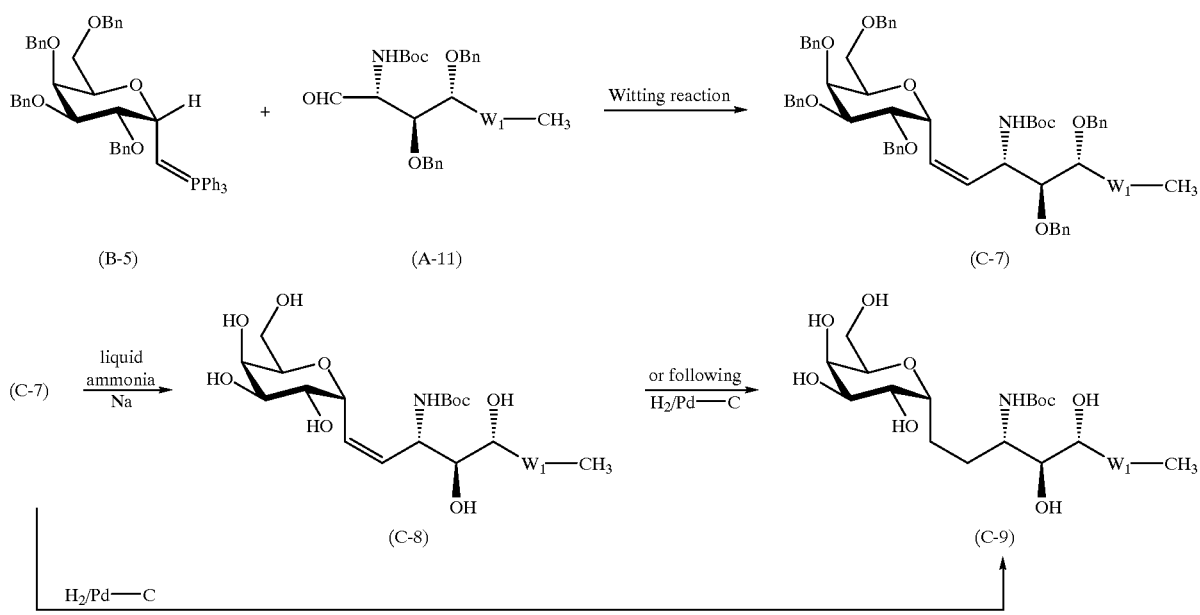

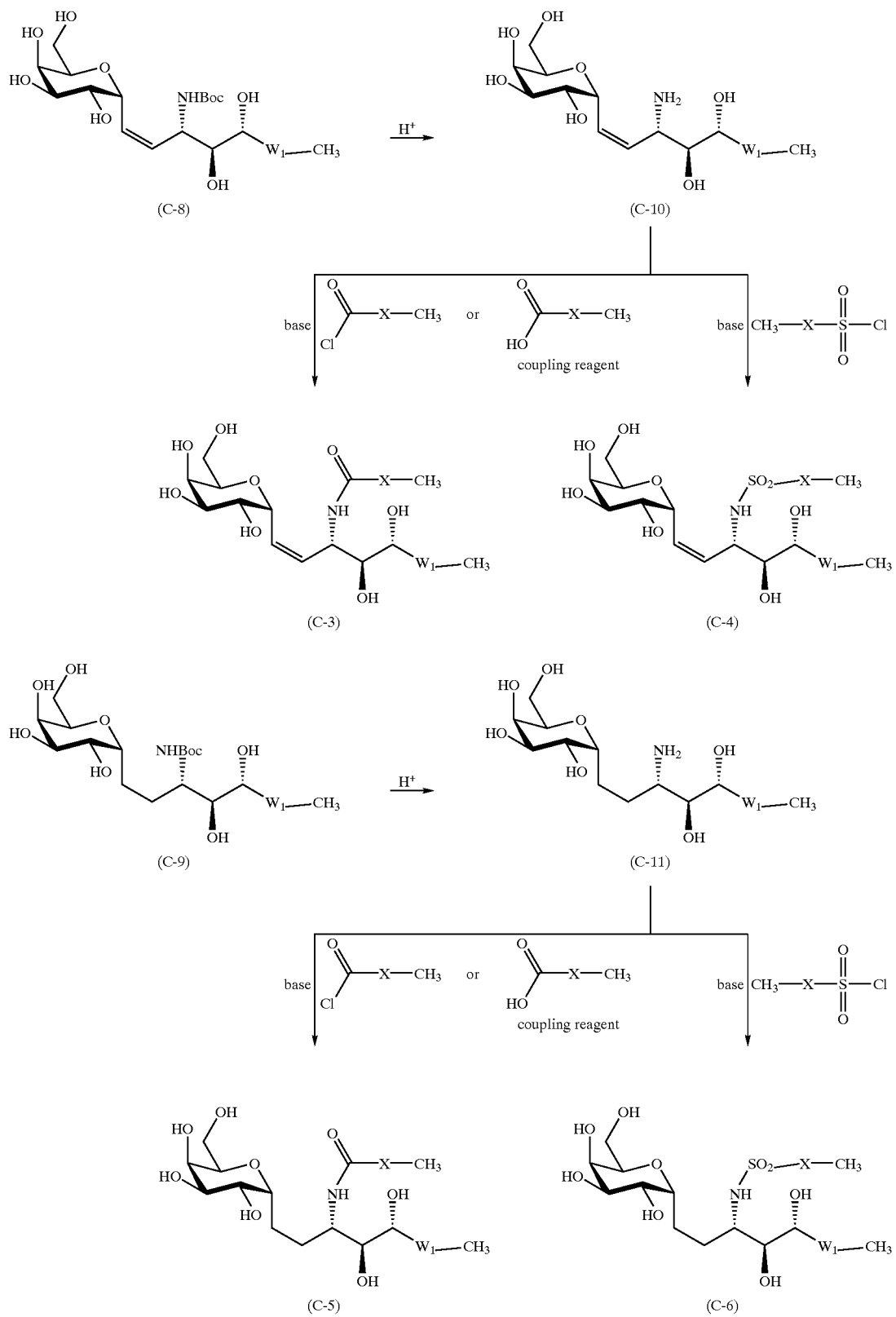
III. The ceramide compound (A-13) which was prepared by the method (A), is glycosylated with the sugar derivatives (C-12) or (C-13) in the presence of base so as cesium carbonate, to yield the compound (C-14) or (C-15).

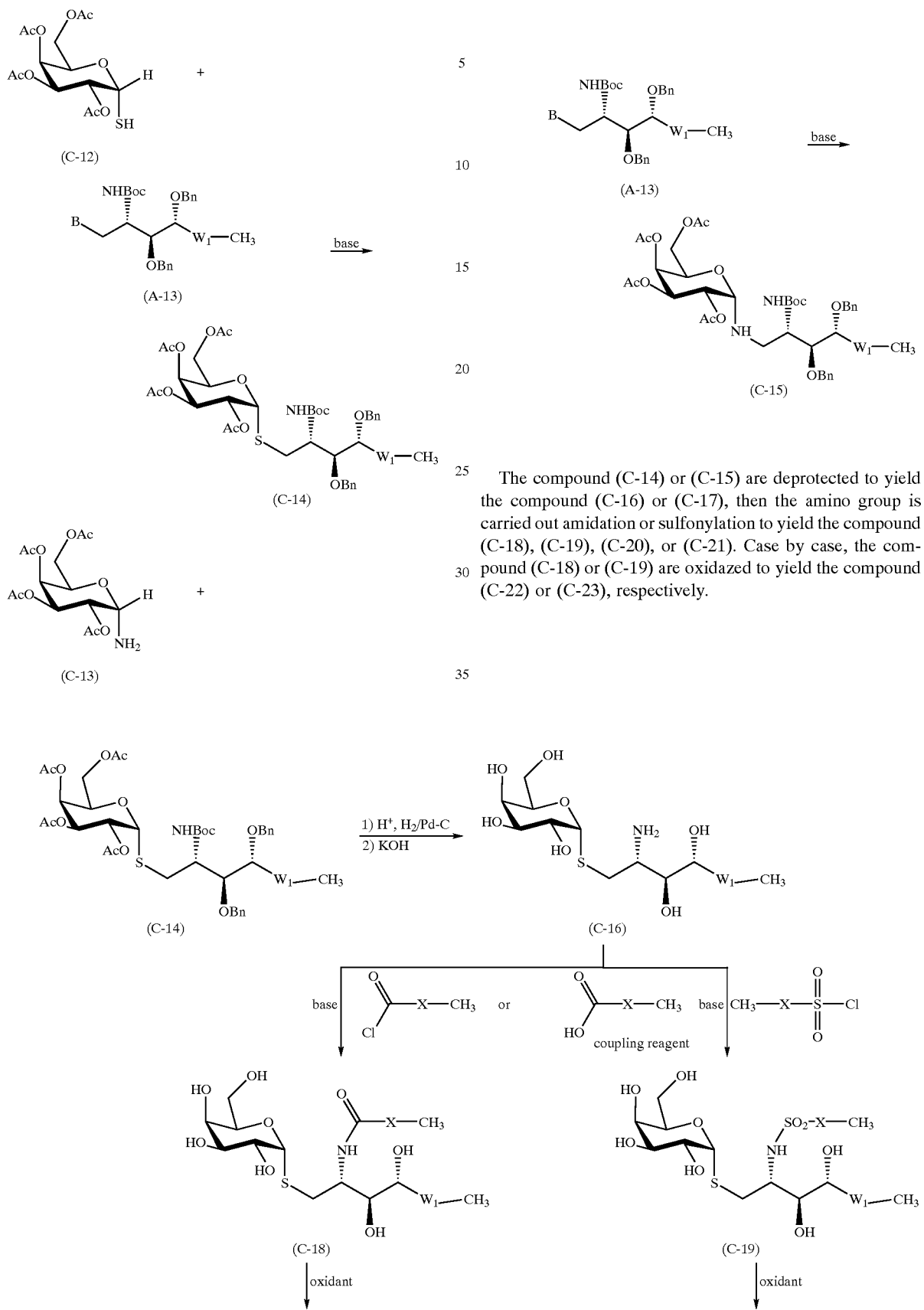
The compound (C-14) or (C-15) are deprotected to yield the compound (C-16) or (C-17), then the amino group is carried out amidation or sulfonylation to yield the compound (C-18), (C-19), (C-20), or (C-21). Case by case, the compound (C-18) or (C-19) are oxidazed to yield the compound (C-22) or (C-23), respectively.

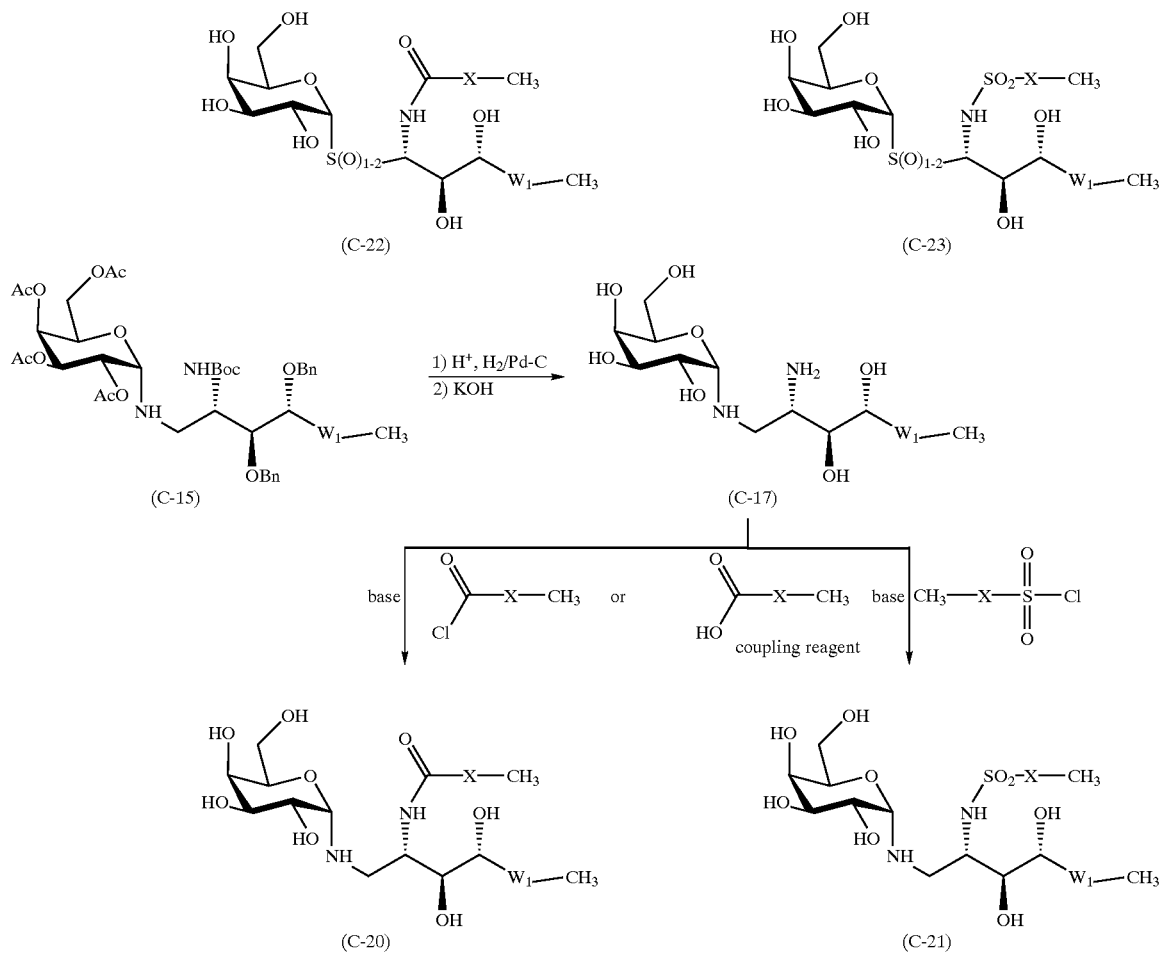

(D) Modification of Primary Hydroxy Group of the Suger Moiety

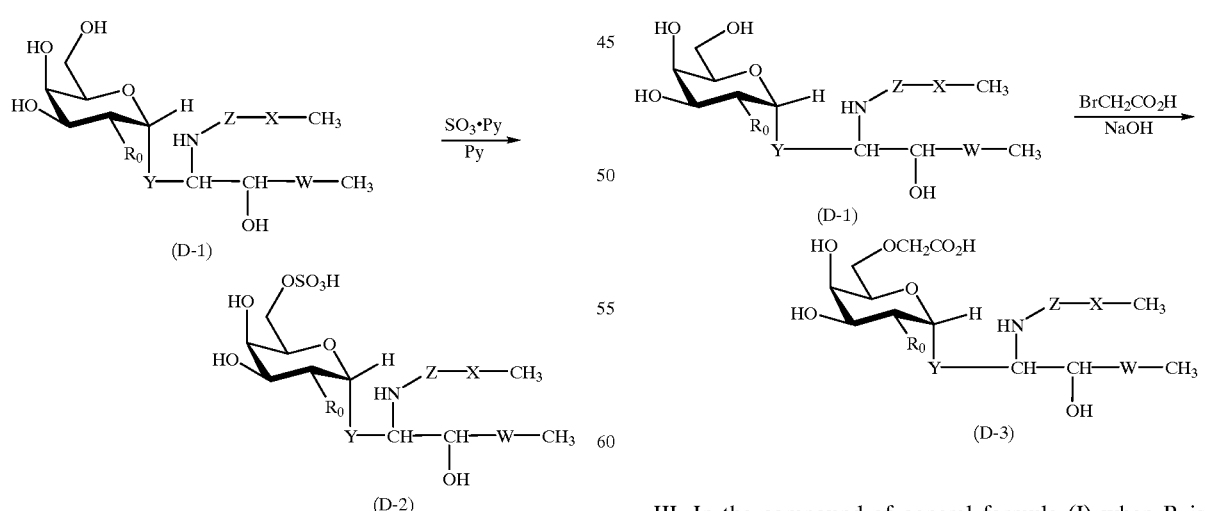

II. In the compound of general formula (I) when R is $CH_2OCH_2CO_2H$, the compound (D-1) is reacted with $BrCH_2CO_2H$ in the presence of NaOH to yield the compound (D-3).

III. In the compound of general formula (I) when R is $CO_2H$, a primary hydroxy group of the compound (D-1) is converted to carboxylic acid group with oxidant (TEMPO= 2,2,6,6-tetramethyl-1-piperidinyloxy freeradical, etc) to yield the compound (D-4).

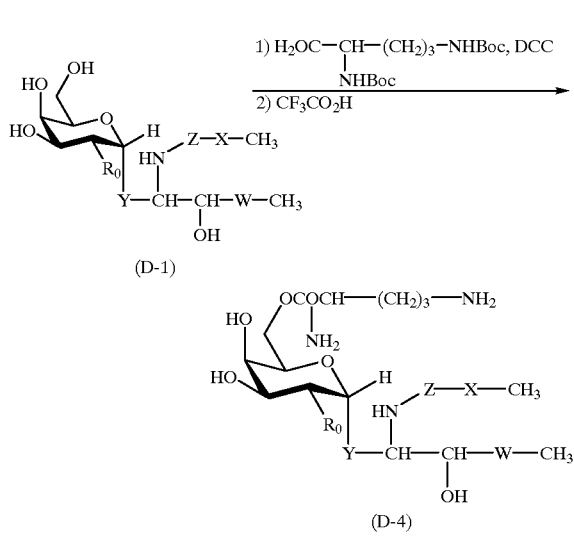

The compounds related to the general formula (I) are exemplified as follows and not restrict the disclosed invention. And, the chemical structure and the analytical value are exhibited as following table.

(1). (3'S,4'S,5'R)-3'-N-Hexacosanoylamino-4',5'-dihydroxy-nonadecane-α-C-D-galactopyranoside (Compound 1)

(2). (3'S,4'S,5'R)-3'-N-Hexacosanoylamino-4',5'-dihydroxy-1'-(E/Z)-nonadecane-α-C-D-galactopyranoside (Compound 2)

(3). (3'S,4'S,5'R)-3'-N-Pentacosanesulfonylamino-4',5'-dihydroxy-nonadecane-α-C-D-galactopyranoside (Compound 3)

(4). (5'S,6'S,7'R)-6',7'-Dihydroxy-5'-N-hexacosanoylamino-(E/Z)-henicos-3'-enyl-α-C-D-galactopyranoside (Compound 4)

(5). (5'S,6'S,7'R)-6',7'-Dihydroxy-5'-N-tetracosanoylamino-(E/Z)-henicos-3'-enyl-α-C-D-galactopyranoside (Compound 5)

(6). (5'S,6'S,7'R)-6',7'-Dihydroxy-5'-N-hexacosanoylamino-henicosane-α-C-D-galactopyranoside (Compound 6)

(7). (5'S,6'S,7'R)-6',7'-Dihydroxy-5'-N-tetracosanoylamino-henicosane-α-C-D-galactopyranoside (Compound 7)

(8). (2'S,3'S,4'R)-3',4'-Dihydroxy-2'-N-hexacosanoylamino-octadecane-1'-thio-yl-α-C-D-galactopyranoside (Compound 8)

(9). (3'S,4'S,5'R)-3'-N-Hexacosanoylamino-4',5'-dihydroxy-nonadecane-α-C-D-(6-O-methylenecarboxylic acid)-galactopyranoside (Compound 9)

(10). (3'S,4'S,5'R)-3'-N-Hexacosanesulfonylamino-4',5'-dihydroxy-nonadecane-α-C-D-(6-O-methylenecarboxylic acid)-galactopyranoside (Compound 10)

(11). (3'S,4'S,5'R)-3'-N-Hexacosanesulfonylamino-4',5'-dihydroxy-nonadecane-α-C-D-galactulonic acid (Compound 11)

| No. | Structure | $^1$H-NMR (Solvent) |
|---|---|---|
| 1 | 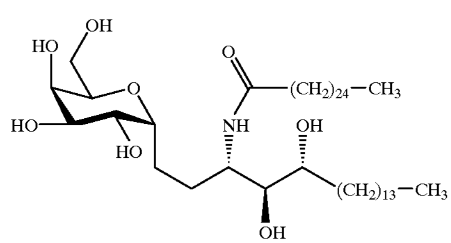 | (CDCl$_3$):<br>0.90 (6H,t,J = 7.4 Hz), 1.29 (74H,m), 1.63–1.65 (2H,m), 1.70–1.86 (2H,m), 2.39 (1H,m), 3.30 (1H,d,J = 8.6 Hz), 3.90–3.52 (1H,m), 3.70–3.74 (3H,m), 3.79 (1H,dd,J = 3.8, 9.0 Hz), 3.80–3.92 (2H,m), 4.11 (1H,d,J = 8.3 Hz), 5.89 (2H,m) |
| 2 | 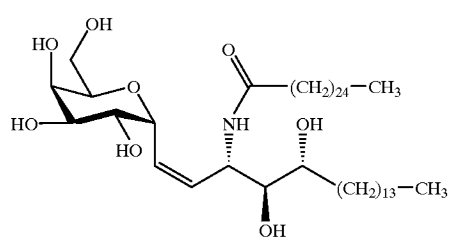 | (CD$_3$OD):<br>0.88 (6H,t,J = 6.8 Hz), 1.25 (72H,m), 1.45–1.60 (4H,m), 2.04 (2H,m), 3.42 (1H,m), 3.60(2H,m), 3.89 (2H,m),4.20–4.55 (7H,m), 5.70 (2H,m) |
| 3 | 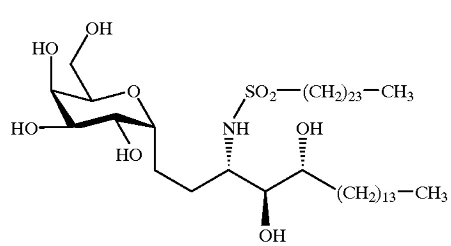 | (CDCl$_3$):<br>0.88 (6H,t), 1.19–1.86 (82H,m), 3.08 (4H,m), 3.49–5.03 (9H,m) |

-continued

| No. | Structure | ¹H-NMR (Solvent) |
|---|---|---|
| 4 | 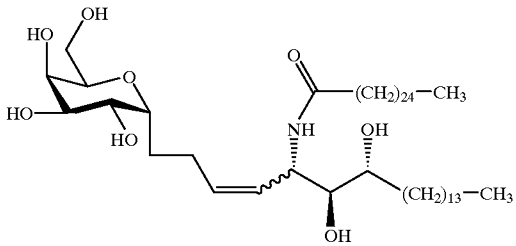 | (DMSO): 0.85 (6H,t,J = 6.8 Hz), 1.20–1.40 (72H,m), 1.40–1.60 (4H,m), 2.02 (2H,m), 3.45 (1H,m), 3.57–3.70 (2H,m), 4.16 (1H,d,J = 6.4 Hz), 4.27 (1H, d,J = 4.4 Hz), 4.42 (1H,m), 4.52 (1H,m), 4.64 (2H,t,J = 4.1 Hz), 4.80 (1H,m), 5.30–5.43 (2H, m), 7.67 (1H,d,J = 7.3 Hz) |
| 5 | 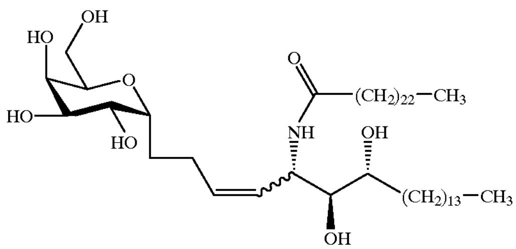 | (CDCl$_3$): 0.85 (6H,t,J = 6.8 Hz), 1.20–1.30 (68H,m), 1.40–1.60 (4H,m), 2.02 (2H,m), 3.45 (1H,m), 3.60–3.70 (2H,m), 4.18 (1H,d,J = 6.4 Hz), 4.27 (1H,d, J = 4.4 Hz), 4.42 (1H,m), 4.48 (1H,m), 4.64 (2H, t,J = 4.1 Hz), 4.85 (1H,m), 5.38–5.43 (2H,m), 7.67 (1H,d,J = 7.3 Hz) |
| 6 | 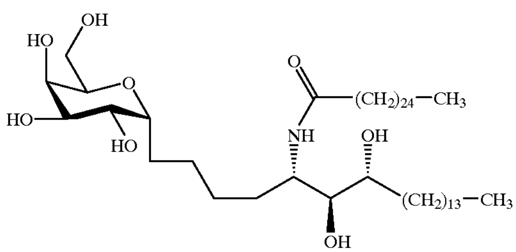 | (DMSO): 0.85 (6H,t,J = 6.8 Hz), 1.20–1.40 (72H,m), 1.40–1.64 (4H,m), 2.22 (2H,m), 3.29–3.39 (3H,m), 3.65 (1H,dd,J = 5.37, 2.4 Hz), 4.20 (1H,d, J = 6.4 Hz), 4.30 (1H,d,J = 4.4 Hz), 4.42 (1H,m), 4.53 (1H,m), 4.60 (2H,t,J = 4.2 Hz), 4.78 (1H,m), 7.62 (1H,d,J = 7.3 Hz) |
| 7 | 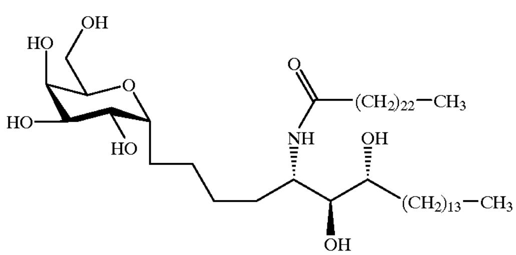 | (DMSO): 0.85 (6H,t,J = 6.8 Hz), 1.23–1.35 (68H,m), 1.40–1.64 (4H,m), 2.50–2.67 (2H,m), 3.05–3.19 (3H, m), 3.65 (1H,m), 4.18 (1H,d,J = 6.4 Hz), 4.25 (1H, d,J = 4.4 Hz), 4.42 (1H,m), 4.18 (1H,m), 4.64 (2H, t,J = 4.1 Hz), 4.90 (1H,m), 7.10 (1H,m) |
| 8 | 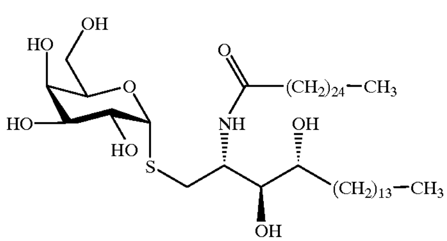 | (CDCl$_3$): 0.86 (3H,t), 1.20–1.85 (74H), 1.94–2.13 (6H, brs), 2.65–3.30 (4H,m), 3.44–5.98 (11H,m) |
| 9 | 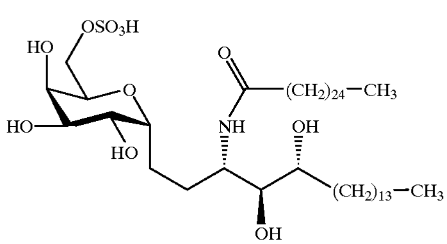 | (DMSO): 0.85 (6H,t), 1.20–1.30 (68H,m), 1.32–1.50 (2H, m), 3.19 (1H,m), 3.21 (1H,d,J = 8.7 Hz), 3.27–3.36 (5H,m), 3.80 (1H,dd,J = 8.4, 4.4 Hz), 4.27 (1H,m), 4.32–4.80 (5H,m) |

-continued

| No. | Structure | $^1$H-NMR (Solvent) |
|---|---|---|
| 10 | (structure) | (DMSO):<br>0.88 (6H,m), 1.20–1.32 (72H,m), 1.45–1.70 (6H, m), 2.12 (2H,m), 3.58 (4H,m), 3.95 (2H,m), 4.25–4.60 (7H,m), 5.70(2H,m) |
| 11 | (structure) | (CD$_3$OD):<br>0.90 (6H,m), 1.19–1.42 (76H,m), 1.58 (4H,m), 1.70 (2H,m), 3.48–4.33 (8H,m) |

The compounds which are described general formula (I) in the present invention or the pharmaceutically acceptable salts can be administered to human or mammal. And the compounds can be formed injections, powders, granules, tablets, capsules, troches, dry-syrups, liposome prepapations etc by known technique to preparation or it's own. The appropriate dose and dosage times, that of the compound pf the present invention, must be determined by the conditions of a patient, age, body weight etc.

PHARMACOLOGICAL EXPERIMENT

A experimental example of anti-tumor activity and immunostimulating activity is described as follows:

Experiment 1: Lymphocyte mixed culture reaction.

The pancreatic cells of BALB/C mouse were regulated to a concentration of 2×10$^6$ cells/ml with a culture medium of 10% FCS RPMI 1640, respectively. These cells (100 ul/well) and a sample (10 ul/well) were plated in a 96 well round-bottomed plate and cultured for 3 days under the condition of 37° C. and 5% CO$_2$. Then, 3H-thymidine (3H-TdR) was added in a dose of 0.5 uCi/well. After 6 hours, the cells were harvested and subjected to the measurement of the uptake of 3H-TdR by a liquid scintillation counter. Thus, the DNA synthesis of pancreatic lymphocyte of mouse was measured was measured. The results are described as following table 1.

TABLE 1

DNA synthesis of pancreatic lymphocyte of mouse

| Compound No. | Concentration (ng/mL) | Increase of DNA synthesis (%) |
|---|---|---|
| 1 | 1 | 54.6 |
| 8 | 1 | 35.4 |

Experiment 2: Tumor metastasis inhibitory activity against B16 mouse melanoma.

B16 mouse melanoma cells (5×105 cells) were injected into tail vein of C57BL/6 mouse (7 weeks old). Next day, a solution which was prepared with several concentrations of the compound were injected into tail vein. After 14 days from the injection of B16 mouse melanoma cells, the mouse were killed under anesthesia and the lungs were excised. Numbers of nodules on the lung surface were measured and tumor metastasis inhibitory effects were estimated by comparison with control groups which were not injected the compound. The results are described as following table 2.

TABLE 2

Metastasis of B16 mouse melanoma cells

| Compound No. | Dose (mg/kg, p.o.) | Inhibition of metastasis (%) |
|---|---|---|
| 1 | 0.001 | 65.3 |
| 8 | 1 | 80.8 |

EXAMPLE

The following examples are provided only for the purpose of the compound and not restrict the disclosed invention.

Referential Example: 1

(2S,3S,4R)-2-Azide-1-o-triphenylmethyl-1,3,4-octadecanetriol (Compound 15)

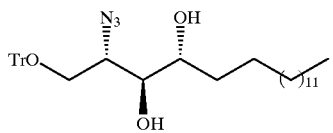

(2S,3S,4R)-2-Azide-1,3,4-octadecanetriol (491 mg) was dissolved in pyridine (15 mL), followed by addition of triphenylmethylchloride (439 mg) and dimethyl aminopyridine (5 mg), then the reaction mixture was stirred for 8 h at 70° C. The reaction mixture was diluted with ethylacetate, and washed by water, satd. Na$_2$CO$_3$, brine, respectively. The organic layer was dried (Na$_2$SO$_4$), filtered, and concentrated. The residue was purified by silicagel column chromatography (n-hexane AcOEt=4:1), and the object compound 15 (421 mg) was obtained.

Mass (ESI) m/z: 609 [(M+Na+H)$^+$].

IR (neat, cm$^{-1}$): 3412, 2908, 2848, 1449, 1215, 1071.

$^1$H-NMR (CDCl$_3$): 0.88(t, 3H, J=7.32, 6.35 Hz), 1.24~1.56(m, 26H), 1.81(d, 1H, J=5.37 Hz), 2.35(d, 1H, J=5.37 Hz), 3.40~3.66(m, 5H), 7.23~7.48(m, 15).

Referential Example: 2

(2S,3S,4R)-2-Azide-1-o-triphenylmethyl-3,4-di-o-benzyl-1,3,4-octadecanetriol (Compound 16)

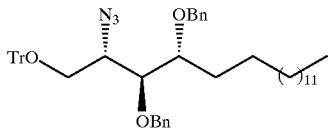

(2S,3S,4R)-2-Azide-1-o-triphenylmethyl-1,3,4-octadecanetriol (Compound 15 ; 586 mg) was dissolved in dimethylformamide (5 mL), followed by addition of sodium hydroxide (105 mg) at 0° C., then stirred for 40 min at room temperature. Subsequently, the reaction mixture was added benzyl bromide (0.25 mL), and stirred for 18 h at room temperature.

The reaction mixture was poured into ice water, then extracted with ethylacetate, washed by water and brine, dried (Na$_2$SO$_4$), and concentrated. The resulting residue was purified by silicagel column chromatography (n-hexane: AcOEt=30:1), and the object compound 16 (574 mg) was obtained.

Mass (ESI) m/z: 783 [(M$^+$+H$_2$O+H$^+$−1)$^+$].

IR (neat, cm$^{-1}$): 2914, 2848, 1449, 1086, 1029, 744.

$^1$H-NMR (CDCl$_3$): 0.88(t, 3H, J=7.32, 6.35 Hz), 1.23~1.54(m, 26H), 3.34~3.76(m, 5H), 4.41~4.58(m, 4H), 7.07~7.45(m, 25H).

Referential Example: 3

(2S,3S,4R)-2-Amino-1-o-triphenylmethyl-3,4-di-o-benzyl-1,3,4,-octadecanetriol (Compound 17)

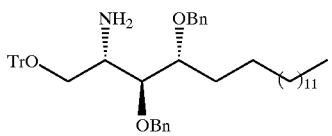

(2S,3S4R)-2-Azide-1-o-triphenylmethyl-3,4-di-o-benzyl-1,3,4-octadecanetriol (Compound 16; 153 mg) was dissolved in THF (3mL), followed by addition of lithium aluminum hydride (11 mg) at 0° C., then stirred for 30 mm at 0° C. and the temperature was raised to room temperature over 2 h. The reaction mixture was added water and filtered on celite pad. The filtrate was extracted with ethyl acetate, washed with brine, dried (N$_{a2}$SO$_4$), concentrated. The resulting residue was purified by silicagel column chromatography (n-hexane: AcOEt=2:1), and the object compound 17 was obtained.

Mass (ESI) m/z: 739 [(M$^+$+H+1)$^+$].

IR (neat, cm$^{-1}$): 3052, 3022, 2914, 1737, 1449.

$^1$H-NMR (CDCl$_3$): 0.88(t, 3H, J=6.83, 6.89 Hz), 1.24~1.63(m, (CH$_2$)$_{13}$), 3.13~3.14(m, 2H), 3.46~3.66(m, 3H), 4.39~4.67(m, 4H), 7.10~7.42(m, 25H).

Referential Example: 4

(2S,3S,4R)-2-(Hexacosanoylamino)-1-o-triphenylmethyl-3,4-di-o-benzyl-1,3,4,-octadecanetriol (Compound 18)

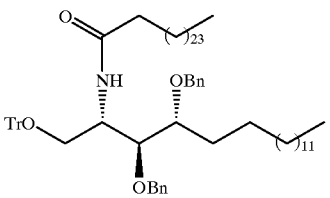

Cerotic acid (56 mg) was dissolved in DMF (4 mL), followed by addition of 1-hydroxy-1H-benzotriazole monohydrate (21 mg), N-ethylmorpholine (0.02 mL), and 1-[3-(dimethylamino)propyl]-3-ethyl carbodiimide hydrochloride (27 mg), then stirred for 1 h at room temperature. Then (2S,3S ,4R)-1-amino-1-o-triphenylmethyl-3,4-di-o-benzyl-1,3,4,-octadecanetriol (Compound 17; 104 mg) was added, stirred for 4 h at room temperature, and further stirred for 2 h at 60° C. The reaction mixture was diluted with ethyl acetate, then washed with 5% aq.HCl, water, 5% aq.NaOH, water, sat.NH$_4$Cl. and brine in turn. The organic layer was dried (Na$_2$SO$_4$) and concentrated. The resulting residue was purified by silicagel column chromatography (n-hexane: AcOEt=10:1), and the object compound 18 (135 mg) was obtained.

Mass (ESI) m/z: 1157 [(M+K+H)$^+$].

IR (neat, cm$^{-1}$): 3022, 2902, 2848, 1656, 1494, 1452.

$^1$H-NMR (CDCl$_3$): 0.88(t, 6H, J=6.83, 6.84 Hz), 1.24~1.57(m, 72H), 1.92(t, 2H, J=7.81, 7.33 Hz), 3.29(dd, 1H), 4.28(m, 1H), 3.46~3.49(m, 2H), 3.83(dd, 1H, J=6.84, 2.93 Hz), 4.99~4.80(abq+S, 4H, J=11.71, 11.72 Hz), 5.58(d, 1H, J=8.79 Hz), 7.20~7.38(m, 25H).

Referential Example: 5

(2S,3S,4R)-2-(Pentacosanesulfonamide)-1-o-triphenylmethyl-3,4-di-o-benzyl-1,3,4,-octadecanetriol (Compound 19)

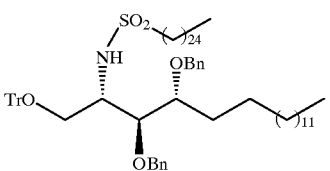

(2S ,3S,4R)-2-Amino-1-o-triphenylmethyl-3,4-di-o-benzyl-1,3,4,-octadecanetriol (Compound 17; 514 mg) was dissolved in CH$_2$Cl$_2$ (6 mL), followed by addition of triethylamine (0.15 mL) and pentacosanylsulfonylchloride (314 mg) at 0° C., and stirred for 12 h at room temperature. The reaction mixture was added water, then extracted with chloroform (50 mL×2), dried (Na$_2$SO$_4$), filtered, and concentrated. The resulting residue was purified by silicagel column chromatography (n-hexane: AcOEt=10:1), and the object compound 19 (530 mg) was obtained.

IR (neat,cm$^{-1}$): 3274, 2908, 1452, 1323, 1215, 1140, 1068, 753.

$^1$H-NMR (CDCl$_3$): 0.88(6H, t, CH$_3$), 1.18~1.65(72H, m, CH$_2$), 2.80(2H, m, CH$_2$), 3.42(2H, d, CH$_2$), 3.62(1H, m,

Referential Example: 6

(2S,3S,4R)-2-Hexacosanoylamino-3,4-di-o-benzyl-1,3,4,-octadecanetriol (Compound 20)

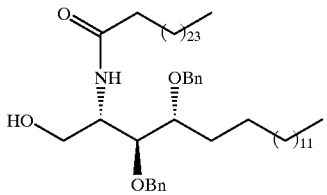

(2S,3S,4R)-2-(Hexacosanoylamino)-1-o-triphenylmethyl-3,4-di-o-benzyl-1,3,4,-octadecanetriol (Compound 18; 117 mg) was dissolved in methanol (1.5 mL), followed by addition of p-toluenesulfonic acid (10 mg), and stirred for 3 h at room temperature. The reaction mixture was diluted with ethyl acetate, and poured into sat. NaHCO$_3$. The organic layer was separated, washed with water, dried (Na$_2$SO$_4$), and concentrated. The resulting residue was purified by silicagel column chromatography (n-hexane: AcOEt=3:1), and the object compound 20 (58 mg) was obtained. m.p.=67–68° C.

Mass (ESI) m/z: 877 [(M+H+1)$^+$].

IR (neat, cm$^{-1}$): 3460, 2908.

$^1$H-NMR (CDCl$_3$): 0.88(t, 6H, J=6.84, 6.35 Hz), 1.25~1.69(m, 72H), 1.97~2.02(m, 2H), 3.05~3.07(m, 1H), 3.59~3.62(m, 2H), 3.68~3.72(m, 2H), 3.98~4.01(m, 1H), 4.14~4.16(m, 1H), 4.45~4.72(abq, 2H, J=11.71, 11.23 Hz), 4.64(abq, 2H, J=11.23, 11.24 Hz), 6.04(d=1H, J=8.31 Hz), 7.28~7.39(m, 10H).

Referential Example: 7

(2S,3S,4R)-2-Hexacosanoylamino-3,4-dibenzyloxy-octadecanal (Compound 21)

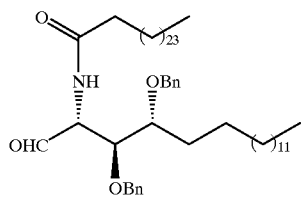

Oxaryl chloride (0.45 mL) was dissolved in CH$_2$Cl$_2$ (3 mL), followed by addition of dimethylsulfoxide (0.15 mL) at −78° C., and stirred for 20 min. Subsequently, a solution, that (2S,3S,4R)-2-hexacosanoylamino-3,4-di-o-benzyl-1,3,4-octadecanetriol (Compound 20; 263 mg) was dissolved in CH$_2$Cl$_2$ (2 mL), was added and stirred at 78° C., and after a temperature of the reaction mixture was raised to room temperature, was stirred for 30 min. The reaction mixture was poured into ice water, then extracted with ethyl acetate, washed with water and brine, dried (N$_{a2}$SO$_4$), filtered, and concentrated. The resulting residue was purified by silicagel column chromatography (n-hexane; AcOEt=4:1) and the object compound 231 (189 mg) was obtained.

Mass (ESI) m/z: 875 [(M+H+1)$^+$].

IR (neat, cm$^{-1}$): 3382, 2902, 1710, 1499, 1048, 741.

$^1$H-NMR (CDCl$_3$): 0.88(t, 6H, J=6.83, 6.35 Hz), 1.25~1.71(m, 72H), 1.99~2.02(m, 2H), 3.60(q, 1H), 3.92 (dd, H, J=5.37, 2.44 Hz), 4.49~4.61(2 abq, 4H), 4.93(dd, 1H, J=7.32, 2.44 Hz), 6.04(d, 1H, J=7.32 Hz), 7.26~7.36(m, 10H), 9.66(S, 1H).

Referential Example: 8

(Compound 22)

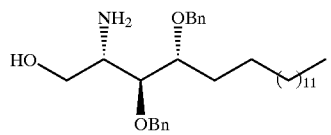

The compound 16 (1.48 g) was dissolved in CH$_2$Cl$_2$/H$_2$O (2:1, 12 mL), followed by addition of p-toluenesulfonic acid (380 mg), then the mixture was stirred for 16 h at room temperature. The reaction mixture was extracted with ethyl acetate (30 mL), washed with water, dried (Na$_2$SO$_4$), filtered, and concentrated. The residue was dissolved in THF/H$_2$O (5:1, 15 mL), followed by addition of triphenylphosphine (700 mg), then the mixture was refluxed for 2 h. The reaction mixture was concentrated, and the residue was purified by silicagel column chromatography (CHCl$_3$: MeOH=20:1). The object compound 22 (520 mg) was obtained.

Mass (ESI) m/z: 497 [M$^+$].

$^1$H-NMR (CDCl$_3$): 0.88(3H, t, J=11.8 Hz), 1.18~1.36 (24H, m), 1.42~1.73(2H, m), 3.40~3.65(5H, m), 4.27~4.70 (4H, m), 7.21~7.38(10H, m).

Referential Example: 9

(Compound 23)

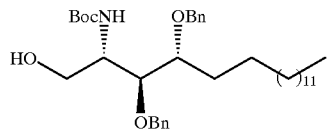

The compound 22 (1.0 g) was dissolved in THF (10 mL), followed by addition of triethylamine (0.33 mL) and di-t-buthyldicarbonate (0.55 mL) at 0° C., then the mixture was stirred for 4 h. The reaction mixture was concentrated, and the resulting residue was purified by silicagel column chromatography (n-hexane: AcOEt=10:1). The object compound 23 (960 mg) was obtained.

Mass (ESI) m/z: 585 [(M+H)$^+$].

$^1$H-NMR (CDCl$_3$): 0.88(3H, m), 1.26~1.30(24H, m), 1.43(9H, s), 1.64~1.70(2H, m), 2.80(1H, bs), 3.64~4.05(5H, m), 4.53~4.75(4H, m), 5.10(1H, m), 7.27~7.38(10H, m).

Referential Example: 10

(Compound 24)

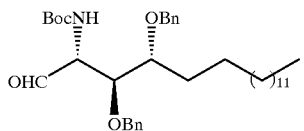

To a solution of dimethylsulfoxide (0.77 mL) and CH$_2$Cl$_2$ (10 mL) was added 2M CH$_2$Cl$_2$ solution of oxalyl chloride (4.0 mL) at −78° C. and the mixture was stirred for 15 min, then a solution of compound 23 (1.17 g) and CH$_2$Cl$_2$ was added and stirred for 30 min. Subsequently, triethylamine (2.1 mL) was added, and the reaction temperature was raised to room temperature. The reaction mixture was poured into ice water, extracted with ethyl acetate (30 mL), washed with water and brine, dried (N$_{a2}$SO$_4$), filtered, and concentrated. The resulting residue was purified by silicagel column chromatography (n-hexane: AcOEt=20:1), and the object compound 24 (680 mg) was obtained.

Mass (ESI) m/z: 583 [M$^+$].

$^1$H-NMR (CDCl$_3$): 0.87(3H, m), 1.27~1.31(24H, m), 1.44(9H, s), 3.64~4.08(5H, m), 4.55~4.72(4H, m), 7.27~7.40(10H, m), 9.83(1H, s).

Referential Example: 11

(2S,3S,4R)-3,4-Benzyloxy-2-tert-butoxycarbonylamino-1-methane-sulfonyloxy-octadecanetriol (Compound 25)

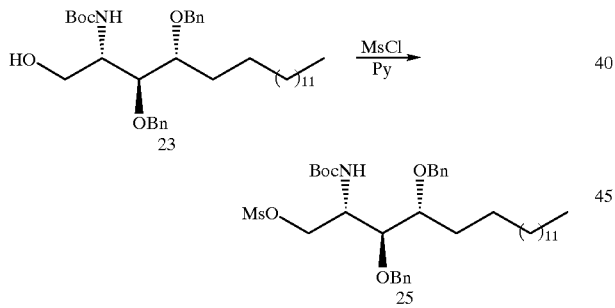

(2S,3S,4R)-3,4-Benzyloxy-2-tert-butoxycarbonylamino-octadecanetriol (Compound 23; 100 mL) was dissolved in pyridine (2 mL), follows by addition of methanesulfonyl chloride (15 μL) at room temperature, then the mixture was stirred for 3 h. The reaction mixture was diluted with ethyl acetate (50 mL), washed with sat.CuSO$_4$ (twice), dried (Na$_2$SO$_4$), filtered, and concentrated. The residue was purified by silicagel column chromatography (n-hexane: AcOEt=10:1), and the object compound 25 (108 mg) was obtained as a colorless oil.

Mass (ESI) m/z: 676 [M+H]$^+$.

$^1$H-NMR (CDCl$_3$): 0.88(3H, t,), 1.26~1.68(35H, m), 2.88 (3H, S), 3.59(1H, m), 3.67(1H, m), 4.05(1H, m), 4.43(2H, m), 4.51~4.82(5H, m), 7.29~7.36(10H, m).

Referential Example: 12

α-(2,3,4,6-Tetrabenzylgalactopyranosyl) methylphosphonium iodide (Compound B-4)

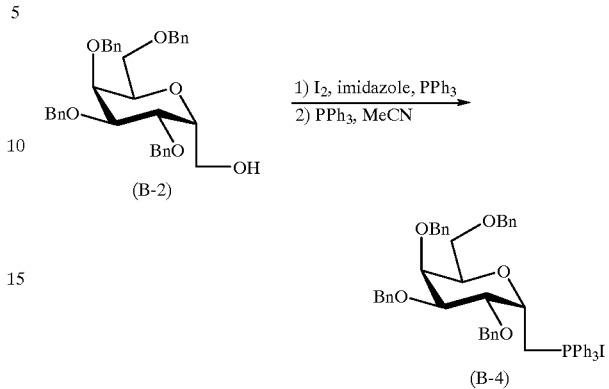

To solution of α-2,3,4,6-tetrabenzylgalactopyranosylmethanol (B-2; 5.2 g), Ms4A (10 g), and benzene (120 mL) was added triphenyl phosphine (3.7 g), imidazole (1.9 g), and iodide (3.6 g), then the mixture was stirred for 1 h at room temperature. The reaction mixture was diluted with ether (150 mL), filtered, and concentrated. The residue was purified by silicagel column chromatography, and the object compound B-4 (2.7 g) was obtained.

Mass (ESI) m/z: 944 [M+H$_2$O].

IR (neat, cm$^{-1}$): 3004, 2914, 1584, 1452, 1357, 1215, 1026, 915.

$^1$H-NMR (CDCl$_3$): 3.30(1H, t, J=8.2 Hz), 3.42(1H, dd, J=8.2, 2.8 Hz), 3.97~4.83(15H, m), 7.17~7.86(35H, m).

Example: 1

Compound 26

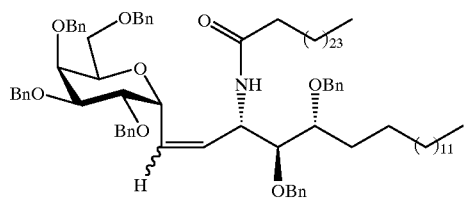

α-(2,3,4,6-Tetrabenzylgalactopyranosyl)methyl phosphonium iodide (B-4; 520 mg) was dissolved in THF: hexamethyl phosphoric triamide (HMPA) (2:1, 30 mL), followed by addition of MS4A (500 mg) and n-BuLi in hexane (0.35 mL) at −40° C., and stirred for 30 min. Subsequently, a solution of 2S,3,S4R)-2-Hexacosanoylamino-3,4-dibenzyloxy-octadecanol (Compound 21; 490 mg) and THF (4.0 mL) was added, then the temperature was raised to −10° C. The reaction mixture was poured into sat.NH$_4$Cl, extracted with ethyl acetate (30 mL×2), washed with water, dried (N$_{a2}$SO$_4$), filtered, and concentrated. The residue was purified by silicagel column chromatography (n-hexane; AcOEt=5:1), and the object compound 26 (110 mg) was obtained.

Mass (ESI) m/z: 1397 [M$^+$+1].

$^1$H-NMR (CDCl$_3$): 0.89(6H, t, J=7.2 Hz), 1.10~1.82(76H, m), 1.58~1.65(2H, m) 3.40(1H, dd, J=4.8, 8.2 Hz), 3.52~3.64(2H, m), 3.88(1H, dd, J=4.6, 10.2 Hz), 3.80~5.10 (14H, m), 6.09(1H, d, J=8.8 Hz), 6.63(2H, m), 7.11~7.36 (30H, m).

Example: 2

(3'S,4'S,5'R)-3'-N-Hexacosanoylamino-4',5'-hydroxy-nonadecane-α-c-D-garactosylanoside (Compound 1)

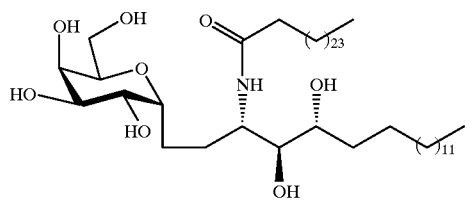

Compound 26 (110 mg) was dissolved in ethanol (10 mL), followed by addition of 20% palladium hydroxide (20 mg) and 4-methylcyclohexene (1.0 mL), and refluxed for 6 h under $H_2$ atomospher. The mixture was filtred and concentrated, then the residue was purified by silicagel column chromatography (chloroform: methanol=5:1). As a result, the object compound 1 (2.1 mg) was obtained.

Mass (ESI) m/z: 855 [M+−H].

Example: 3

Compound 5

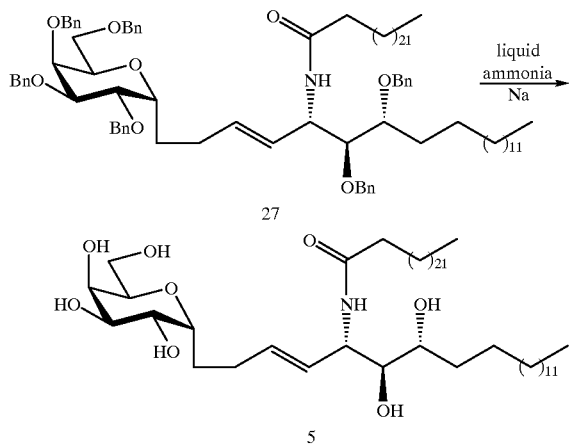

To a solution of liquid ammonia added compound 27 (100 mg/ether 2 mL; 5 mL) at −78° C. Subsequently, the mixture was added a sodium until a color of the solution turned blue, and stirred for 1 h at −78° C. Then, ammonium chloride was added and stand over at room temperature. The reaction mixture was diluted with THF (30 mL), filtered, and concentrated. The residue was purified by silicagel column chromatography (CHCl₃: MeOH=10:1), and the object compound 5 (35 mg) was obtained (54.3% yield).

IR (neat, cm⁻¹): 3400, 2930, 2860, 1638, 1100.

Example: 4

Compound 7

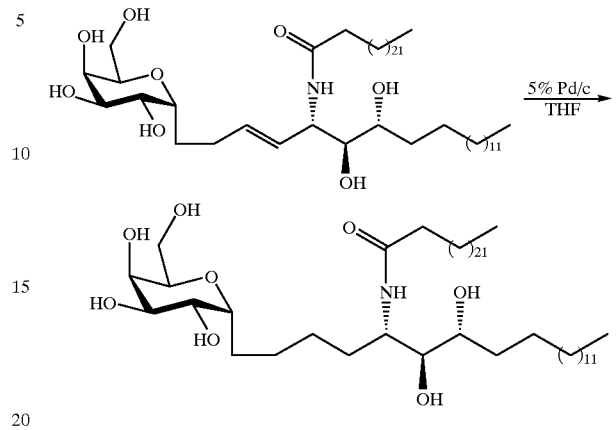

The compound 5 (25 mg) was dissolved in THF (2 mL), followed by addition of 5% palladium carbon (1 mg), and stirred for 40 min at room temperature under $H_2$ atomospher. The reaction mixture was filtered and concentrated, then the residue was purified by silicagel column chromatography (CHCl₃: MeOH=10:1). As a result, the object compound 7 (10 mg) was obtained as a white solid (40% yield).

Mass (ESI) m/z: 855 [M+−2].
IR (neat, cm⁻¹): 3352, 2902, 1593, 1467, 1206.

Referential Example: 13

Compound 28

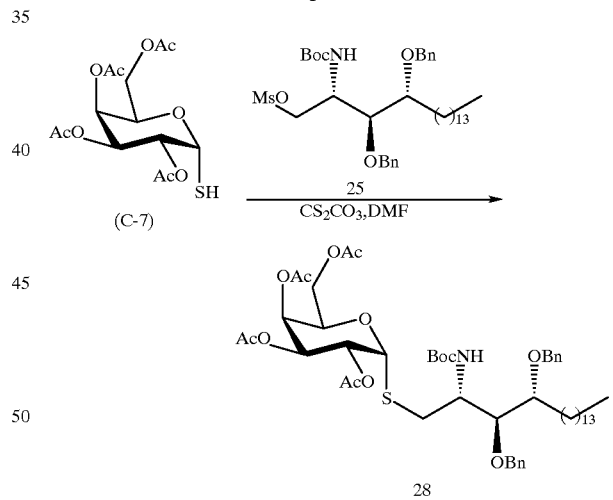

2,3,4,6-Tetra-o-acetyl-1-thio-α-D-galactopyranose (c-7; 70 mg) was dissolved in DMF (5 mL), followed by addition of cesium carbonate (63 mg) and the compound 25 (108 mg), and stirred for 3 h at 80° C. The reaction mixture was diluted with ethyl acetate (50 mL), washed with water (twice), dried (Na₂SO₄), filtered, and concentrated. The residue was purified by silicagel column chromatography (n-hexane: AcOEt=10:1), and the object compound 28 (28 mg) was obtained as a colorless oil.

Mass (ESI) m/z: 944 [M+H]+.
IR (neat, cm³¹ ¹): 3370, 2914, 1746, 1497, 1368, 1224, 1164, 1053, 750.

$^1$H-NMR (CDCl$_3$): 0.88(3H, t), 1.26~1.64(35H, m, CH$_2$), 1.99~2.09(12H, m), 2.88~3.12(2H, m), 3.56~5.67(15H, m), 7.26~7.36(10H, m).

Referential Example: 14

Compound 29

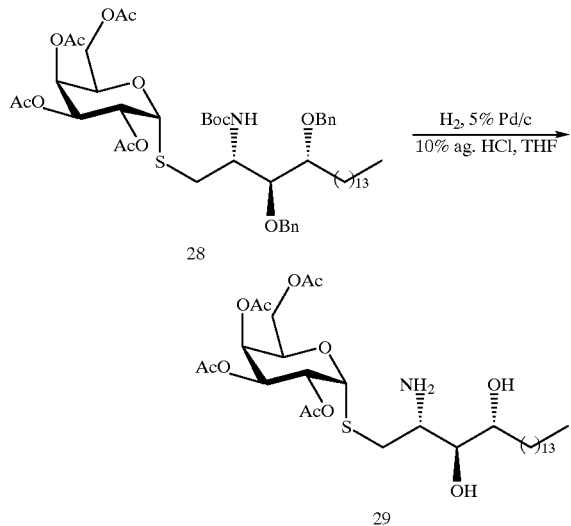

Compound 28 (28 mg) was dissolved in THF (2 mL), followed by addition 10% aq.HCl (1 mL) and 5% palladium carbon (20 mg), and stirred for 6 h at room temperature under H$_2$ atmosphere. The catalyst was filtered off on a celite pad, then the filtrate was dried (Na$_2$SO$_4$), filtered, and concentrated. The object compound 29 (16 mg) was obtained as a pale yellow oil, and the residue was used to next reaction as a crutle product.

Example: 5

Compound 8

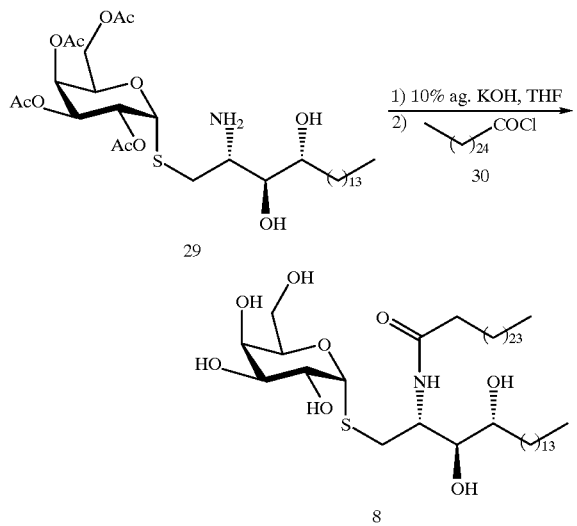

The compound 29 (16 mg) was dissolved in THF (2 mL), followed by addition 10% aq.KOH (1 mL), and stirred for 1 h at room temperature. The reaction mixture was cooled at 0° C. acid chloride (Compound 30; 0.4 mL) was added and stirred for 15 min. The mixture was diluted with THF (10 mL), dried (Na$_2$SO$_4$), filtered, and concentrated. The residue was purified by silicagel column chromatography (CHCl$_3$: MeOH=5:1), and the object compound 8 (7 mg) was obtained as a colorless solid.

Mass (ESI) m/z: 875[M+H]$^+$.

Example: 6

Compound 9

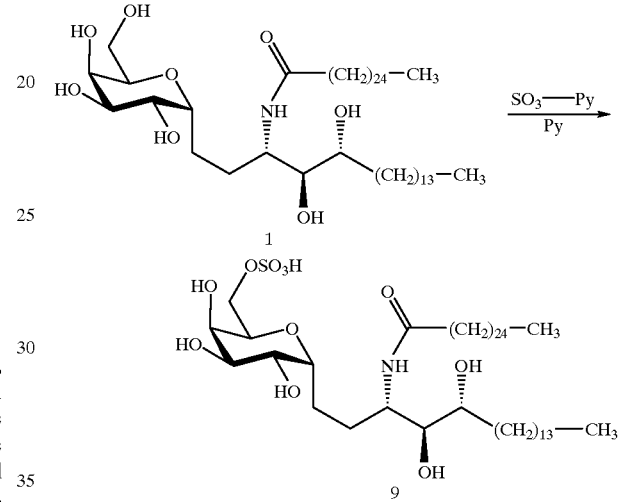

The compound 1 (14 mg) was dissolved in pyridine (0.5 mL), followed by addition of sulfur trioxides pyridine complex (7.6 mg), and stirred for 16 h at room temperature. The reaction mixture was concentrated, and the residue was purified by silicagel column chromatography (H$_2$O: MeOH= 98:2). As a result, the object compound 9 (8 mg) was obtained.

Mass (ESI) m/z: 925[M+H]

Example: 7

Compound 10

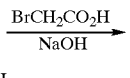

The compound 1 (1.6 mg) was dissolved in THF (1.0 mL), followed by addition of sodium hydroxide (1 mg), and stirred for 30 min at 0° C. Then, the mixture was added bromoacetic acid (1 mg) and stirred for 4 h at 60° C. The reaction mixture was added sat.NH$_4$Cl (200 mL) and concentrated. The residue was purified by short column, and the object compound 10 (0.8 mg) was obtained.

Mass (ESI) m/z: 914[M+H].

Example: 8

The compound 1 (4.5 mg) was dissolved in acetonitre (1 mL), followed by addition of 2,2,6,6-tetramethyl-1-piperidinyloxyractical (TEMPO), sodium perchloride, and potassium bromide at 0° C., and stirred for 2 h at room temperature. The reaction mixture was concentrated and purified by short column, then the object compound 11 (2.8 mg) was obtained.

Mass (ESI) m/z: 869 [M+H]$^+$.

$^1$H-NMR (CDCl$_3$): 0.90(6H, m), 1.19~1.42(76H, m), 1.58(4H, m), 1.70(2H, m), 3.48~4.33(8H, m).

Example: 9

The compound 2 can be prepared by method of the example 3.

Example: 10

The compound 3 can be prepared by methods of the referential example 5, 6, 7 and the example 1,2.

Example: 11–12

The compound 4 and 6 can be prepared by method of the example 1, 2, 3.

What is claimed is:

1. A compound of general formula (I) or a pharmaceutically acceptable salt, (I)

wherein
- W is a saturated or an unsaturated carbon chain from 9 to 17 which can contain a hydroxyl group;
- X is a saturated or an unsaturated carbon chain of carbon number 11 to 25 which can contain a hydroxyl group;
- Y represents —(CH$_2$)$_a$—CH=CH—(CH$_2$)$_{a'}$—, —(CH$_2$)$_a$—S(O)$_{0-2}$—CH$_2$—, —NHCH$_2$—, wherein a and a' each denote an integer of 0–5 and a+a' is 5 or under;
- Z represents —CO—, —SO$_2$—;
- R represents —CH$_2$OH, —CO$_2$H, —CH$_2$OCH$_2$CO$_2$H, —CH$_2$OSO$_3$H; and
- R$_0$ represents —OH, —NH$_2$, —NHAc.

2. A method for preparing a compound having the formula (d), (d)

wherein
- R$_0$ represents —OH, —NH$_2$, —NHAc,
- X is a saturated or an unsaturated carbon chain of carbon number 11 to 25 which can contain a hydroxyl group,
- Z represents —CO—, —SO$_2$—, and
- W is a saturated or an unsaturated carbon chain from 9 to 17 which can contain a hydroxyl group, comprising the steps of:
  reacting a compound of formula (a) in a Wittig reaction (a)

wherein
- R$_1$ represents —O—R$_4$, —O—Si(R$_4$)$_3$, —O—CO—R$_4$;
- R$_5$ represents —O—R$_4$, —O—Si(R$_4$)$_3$, —O—CO—R$_4$, —NAc$_2$, —NHAc;

$R_3$ represents —$PPh_3^+I^-$, —$P(=O)$—$(O-R_4)_2$ wherein $R_4$ represents lower alkyl or phenyl group;

b denotes an integer of 0–5, with a compound of formula (b),

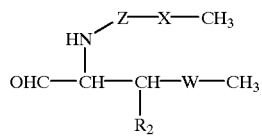

(b)

wherein $R_2$ represents —$O$—$R_4$, —$O$—$Si(R_4)_3$, —$O$—$CO$—$R_4$, wherein $R_4$ represents lower alkyl or phenyl group;

in the presence of a base to produce a compound of the following formula (c),

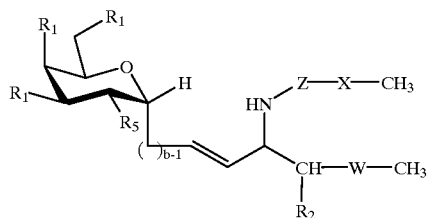

(c)

and deprotecting the compound of formula (c) to produce the compound of formula (d).

3. A method for preparing the compound of claim 1 having the formula (d), comprising the step of:

reacting a compound of formula (a) in claim 2 with a compound of formula (f),

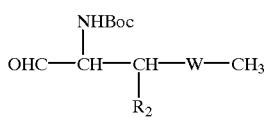

(f)

wherein

Boc represents t-butyloxycarbonyl group, in the presence of a base to produce a compound of formula (g),

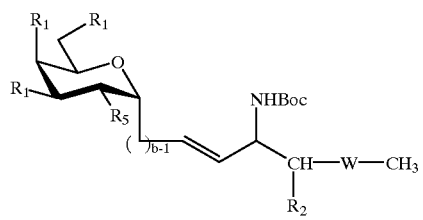

(g)

deprotecting said Boc group followed by amidation or sulfonylation, and further deprotection to produce the compound of formula (d).

4. A method for preparing a compound having the formula (e),

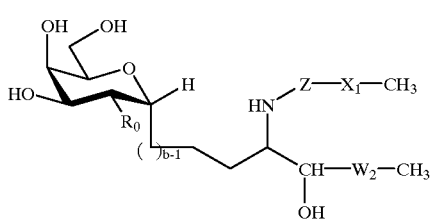

(e)

wherein $X_1$ is a saturated or an unsaturated carbon chain of carbon number 11 to 25 which can contain a hydroxyl group;

$W_2$ is a saturated or an unsaturated carbon chain from 9 to 17 which can contain a hydroxyl group;

$R_0$ represents —$OH$, —$NH_2$, —$NHAc$,

Z represents —$CO$—, —$SO_2$—, and b denotes an integer of 0–5, comprising the steps of:

hydrogenating the compound of formula (g),

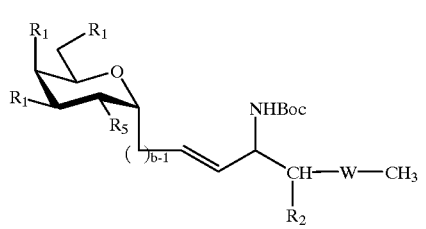

(g)

wherein $R_1$ represents —$O$—$R_4$, —$O$—$Si(R_4)_3$, —$O$—$CO$—$R_4$;

$R_2$ represents —$O$—$R_4$, —$O$—$Si(R_4)_3$, —$O$—$CO$—$R_4$;

wherein $R_4$ represents lower alkyl or phenyl group, $R_5$ represents —$O$—$R_4$, —$O$—$Si(R_4)_3$, —$O$—$CO$—$R_4$, —$NAc_2$, —$NHAc$;

W is a saturated or an unsaturated carbon chain from 9 to 17 which can contain a hydroxyl group, b denotes an integer of 0–5, Boc represents t-butyloxy carbonyl group, with a palladium catalyst Pd/c or Pd(OH)$_2$ deprotecting the Boc group followed by amidation or sulfonylation to produce the compound of formula (e).

5. A method for preparing a compound having the formula (k),

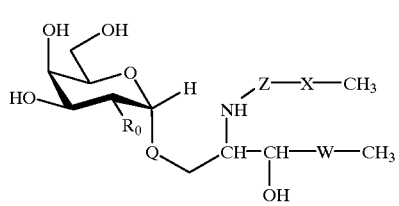

(k)

wherein $R_0$ represents —$OH$, —$NH_2$, —$NHAc$,

X is a saturated or an unsaturated carbon chain of carbon number 11 to 25 which can contain a hydroxyl group, Z represents —CO—, —SO$_2$—, and W is a saturated or an unsaturated carbon chain from 9 to 17 which can contain a hydroxyl group, comprising the step of glycosylating a compound of formula (h),

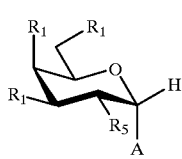

(h)

wherein

R$_1$ represents —O—R$_4$, —O—Si(R$_4$)$_3$, —O—CO—R$_4$;

R$_5$ represents —O—R$_4$, —O—Si(R$_4$)$_3$, —O—CO—R$_4$, —NAc$_2$, —NHAc;

A represents —SH or —NH$_2$, with a compound of formula (i),

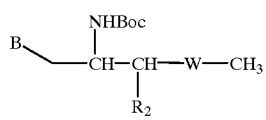

(i)

wherein

R$_2$ represents —O—R$_4$, —O—Si(R$_4$)$_3$, —O—CO—R$_4$; wherein

R$_4$ represents lower alkyl or phenyl group;

B represents a leaving group selected from the group consisting of methanesulfonyloxy group and halogens; Boc represents t-butyloxycarbonyl group, to produce a compound of formula (j),

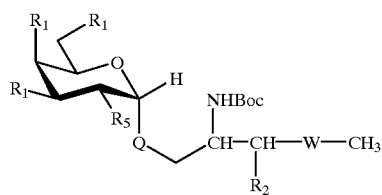

(j)

wherein

Q represents —S— or —NH—, deprotecting the Boc group followed by amidation or sulfonylation, and further deprotection, to produce the compound of formula (k).

6. A method for preparing a compound having the formula (m),

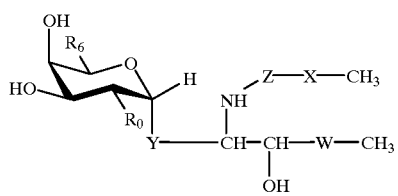

(m)

wherein

R$_0$ represents —OH, —NH$_2$, —NHAc,

X is a saturated or an unsaturated carbon chain of carbon number 11 to 25 which can contain a hydroxyl group, Y represents —(CH$_2$)$_a$—CH=CH—(CH$_2$)$_{a'}$—, —(CH$_2$)$_a$—, —S(O)$_{0-2}$CH$_2$—, —NHCH$_2$—, wherein a and a' each denote an integer of 0–5 and a+a' is 5 or under;

Z represents —CO—, —SO$_2$—,

W is a saturated or an unsaturated carbon chain from 9 to 17 which can contain a hydroxyl group;

R$_6$ represents —CO$_2$H, —CH$_2$OCH$_2$CO$_2$H, —CH$_2$OSO$_3$H, comprising carrying out 2,2,6,6,-tetramethyl-1-piperidinyloxyradical oxidation (TEMPO oxidation), sulfonylation, or carboxymethylation with a compound of formula (l),

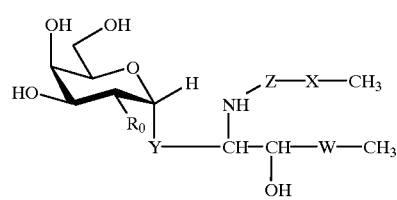

(l)

to produce the compound of formula (m).

7. A pharmaceutical composition effective for use in the treatment of tumor comprising a pharmacologically effective amount of a compound of general formula (I) according to claim 1.

8. An immunostimulating agent containing the compound of general formula (I)

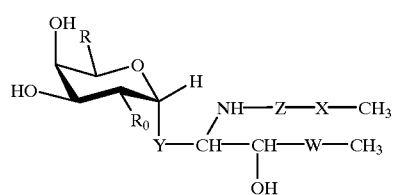

(I)

wherein

W is a saturated or an unsaturated carbon chain from 9 to 17 which can contain a hydroxyl group;

X is a saturated or an unsaturated carbon chain of carbon number 11 to 25 which can contain a hydroxyl group;

Y represents —(CH$_2$)$_a$—CH=CH—(CH$_2$)$_{a'}$—, —(CH$_2$)$_a$—, —S(O)$_{0-2}$CH$_2$—, —NHCH$_2$—, wherein a and a' each denote an integer of 0–5 and a+a' is 5 or under;

Z represents —CO—, —SO$_2$—;

R represents —CH$_2$OH, —CO$_2$H, —CH$_2$OCH$_2$CO$_2$H, —CH$_2$OSO$_3$H; and

R$_0$ represents —OH, —NH$_2$, —NHAc;

and/or the pharmaceutically acceptable salt as an effective ingredient.

* * * * *